United States Patent [19]
Giordano et al.

[11] Patent Number: 5,980,556
[45] Date of Patent: Nov. 9, 1999

[54] SCISSORS-LIKE TOOL FOR A SURGICAL INSTRUMENT AND PROCESS FOR ITS PRODUCTION

[75] Inventors: Nicola Giordano, Villingen-Schwenningen; Theodor Lutze, Balgheim; Dieter Weisshaupt, Immendingen; Paul Wieneke, Reitheim-Weilheim, all of Germany

[73] Assignee: Aesculap AG & Co. KG, Tuttlingen, Germany

[21] Appl. No.: 08/943,168

[22] Filed: Oct. 3, 1997

Related U.S. Application Data

[63] Continuation of application No. PCT/EP96/00750, Feb. 23, 1996.

[30] Foreign Application Priority Data

Apr. 4, 1995 [DE] Germany .......................... 195 12 559

[51] Int. Cl.⁶ .................................................. A61B 17/28
[52] U.S. Cl. ........................................ 606/207; 606/174
[58] Field of Search ................................... 606/207, 206, 606/205, 174, 172

[56] References Cited

U.S. PATENT DOCUMENTS

| | | | |
|---|---|---|---|
| 4,938,214 | 7/1990 | Specht et al. | 606/174 |
| 5,241,968 | 9/1993 | Slater . | |
| 5,352,235 | 10/1994 | Koros et al. . | |
| 5,439,471 | 8/1995 | Kerr | 606/174 |
| 5,584,845 | 12/1996 | Hart | 606/174 |

FOREIGN PATENT DOCUMENTS

| | | |
|---|---|---|
| 0 003 668 | 8/1979 | European Pat. Off. . |
| 0 145 166 | 6/1985 | European Pat. Off. . |
| WO 93/20759 | 10/1993 | Germany . |
| 42 34 884 | 4/1994 | Germany . |
| 43 13 903 | 9/1994 | Germany . |
| 94 19 139 U | 3/1995 | Germany . |
| WO 87/05483 | 9/1987 | WIPO . |
| WO 91/02493 | 3/1991 | WIPO . |
| WO 94/08521 | 4/1994 | WIPO . |

*Primary Examiner*—Michael Buiz
*Assistant Examiner*—Kevin Truong
*Attorney, Agent, or Firm*—Barry R. Lipsitz; Ralph F. Hoppin

[57] ABSTRACT

In order to allow a particularly small construction of a scissors-like tool for a surgical instrument with two interconnected arms which are pivotable elastically between a spread open position and a virtually closed position by engagement of a sleeve over the outside to a greater or lesser extent, this sleeve being axially displaceable relative to and engaging around the scissors-like tool, it is suggested that for forming the arms a rod consisting of elastic material have a diametric, front recess starting from its free end and followed by an additional, diametric, rear recess which is turned through 90° about the longitudinal axis of the rod in relation to the diametric front recess, that the two diametric recesses be connected to one another by transverse recesses extending transversely to the longitudinal axis of the rod, these transverse recesses each extending over oppositely located quadrants of the cross section between the two diametric recesses whereas the two quadrants located therebetween have no such transverse recesses, and that the two arms be bent up permanently into the spread open position in the plane of the front, diametric recess. In addition, a process for the production of such a scissors-like tool is described.

26 Claims, 4 Drawing Sheets

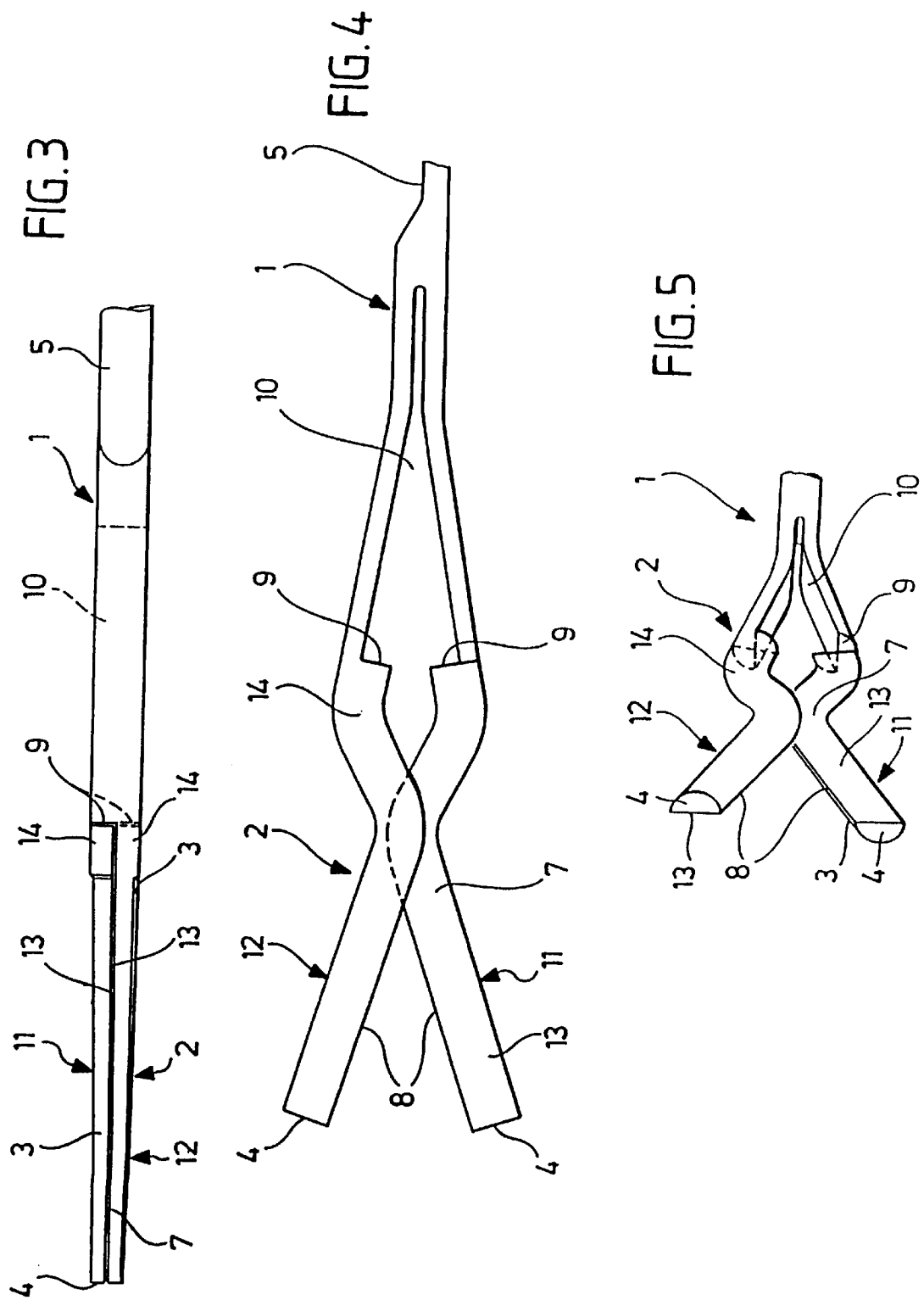

SCISSORS-LIKE TOOL FOR A SURGICAL INSTRUMENT AND PROCESS FOR ITS PRODUCTION

This application is a continuation of International PCT Application No. PCT/EP96/00750 filed on Feb. 23, 1996.

BACKGROUND OF THE INVENTION

The invention relates to a scissors-like tool for a surgical instrument with two interconnected arms which are pivotable elastically between a spread open position and a virtually closed position by engagement of a sleeve over the outside to a greater or lesser extent, this sleeve being axially displaceable relative to and engaging around the scissors-like tool.

Furthermore, the invention relates to a process for the production of such a scissors-like tool.

A scissors-like tool of this type is known, for example, from WO94/08521. In order to be able to use such scissors-like tools in endoscopic operations, it is necessary for very small dimensions to be met; it is, for example, desirable to design the shaft of a corresponding surgical instrument, in which such a scissors-like tool is used, with an external diameter of 2 mm.

It is then practically impossible to use customary, scissorslike tools which comprise two parts articulatedly connected to one another by a closure means.

In the case of the known scissors-like tool of WO94/98521, this scissors-like tool is constructed from two separate parts which are designed like the blades of scissors and are connected permanently to one another in a rear part by means of welding or form-locking. The production is therefore extremely complicated since two individual parts with very small dimensions have to be produced and carefully connected to one another. Moreover, it is almost impossible, in practice, to produce scissors blades of the type shown in this publication with dimensions which are, for example, less than 1 mm in the transverse direction.

SUMMARY OF THE INVENTION

The object of the invention is to design a scissors-like tool of the generic type such that its production is also possible with very small external dimensions.

This object is accomplished in accordance with the invention, in a scissors-like tool of the type described at the outset, in that for forming the arms a rod consisting of elastic material has a diametric, front recess starting from its free end and followed by an additional, diametric, rear recess which is turned through 90° about the longitudinal axis of the rod in relation to the front recess, that the two recesses are connected with one another by transverse recesses extending transversely to the longitudinal axis of the rod, these transverse recesses each extending over oppositely located quadrants of the cross section between the two diametric recesses whereas the two quadrants located therebetween have no such transverse recesses, and that the two arms are bent up permanently into the spread open position in the plane of the front, diametric recess.

It is possible with a scissors-like tool of this type to proceed, for its production, from a simple rod and to work on this by means of various recesses and the bending up of the arms thereby resulting; in this way, a one-piece, scissors-like tool is obtained, with which no connecting operations at all are necessary. It is, therefore, possible to produce a corresponding tool even with very small dimensions; for example, the rod can have an external diameter of 0.7 mm.

It is, furthermore, favorable when the two arms are, in addition, bent towards one another so as to permanently overlap one another in the plane of the rear, diametric recess. As a result, the cutting edges always abut elastically on one another during the cutting movement and ensure a clean cut.

In a preferred embodiment, the rod can have a circular cross section; it is, in particular, a spring wire.

It is provided in a preferred embodiment for the rod to have two lateral, diametrically opposite flattened areas on the outer side, these flattened area forming an acute angle with the front, diametric recess and, together with the inner surface of the front, diametric recess, forming a cutting edge.

In a preferred embodiment of the invention, it is thereby provided for the rod to consist of a pseudoelastic shape memory alloy with a stress-induced martensite formation at body and ambient temperatures. Alloys of this type are known per se (EP 145 166 B1); they are characterized by the fact that they are present in an austenitic state in a specific temperature range when they are not stressed. If they are, on the other hand, stressed, a phase transformation with martensite formation results which is reversible. The phase transformation results isothermally and, as a result, this material allows very considerable, elastic deformations which are greater than the elastic deformations within an unaltered phase. As a result of the phase transformation, a greater, reversible deformation is possible with this material and this is therefore termed a pseudoelastic effect.

Such a material can, for example, be a nickel-titanium alloy. In this respect, this is to be selected such that the pseudoelastic effect described is observed at temperatures which correspond to body temperature and the temperature at which the surgical instrument is used which is, for example, between 15° C. and 45° C.

In a particularly preferred embodiment, it is provided for the rod to be formed by the push and pull rod of a tubular shafted instrument which can be displaced in a tube in axial direction relative thereto. With this development, the scissors-like tool is thus designed in one piece with the push and pull rod which is used, in any case, in tubular shafted instruments for transmitting the opening and closing movement. It is, therefore, no longer necessary to provide special force deflecting members in the tool region or produce connections; the free end of the push and pull rod is remodeled by means of the specified recesses and deformations to form a scissors-like tool.

In addition, it can be provided for the rod to have a bending area with a reduced cross section following the scissors-like tool. As a result, it is possible to arrange such a rod in a bent tube; the bending area with reduced cross section is then arranged in the bent region of the tube accommodating the rod.

In this respect, it can be provided for a flexible hose to be arranged on the rod and within the tube as a sleeve engaging around the scissors-like tool. This can be displaced in axial direction in relation to the rod independently of the bend in the tube and the rod and can be used to open and close the scissors-like tool.

In a modified embodiment, it is provided for the arms to be bent at an angle inwardly in the plane of the front, diametric recess. As a result, it is possible to arrange the two arms at an enlarged cutting angle; this can be of advantage for specific fields of use.

The specified object is accomplished in accordance with the invention by a process for the production of a scissors-like tool which is characterized by the following steps:

a. a diametric, front recess is introduced into a rod consisting of elastic material by a linearly parting tool from the end face of the rod and the rod is thereby separated into two halves in the recess area, b. the rod is turned through 90° about the longitudinal axis of the rod relative to the parting tool at the end of the front recess and two transverse recesses extending over 90° are thereby produced, c. a diametric, rear recess is introduced into the rod by the linearly parting tool, this recess being turned through 90° in relation to the diametric, front recess and extending into the rod towards the rear away from the transverse recesses, d. the arms resulting from the recesses are permanently bent up into a spread open position in the plane of the diametric, front recess.

This makes it clear that the production of the scissors-like tool can be achieved quite simply by means of two different operating steps, namely the introduction of recesses, on the one hand, and the bending up of the resulting arms, on the other hand. The introduction of the recesses results by way of a parting tool, wherein the tool is displaced in longitudinal direction of the rod relative to the rod. Within the path of displacement, tool and rod are turned once through 90° about the longitudinal axis of the rod relative to one another; otherwise, only an advancing of the rod relative to the parting tool takes place in order to produce the recesses. Since this production process is relatively simple and does not require any complicated paths of displacement, it is also possible to provide such a configuration in a rod with very small dimensions.

In order to ensure a mutual biasing of the two arms in the area of the cutting edges, it is further advantageous when the two arms are permanently bent towards one another, in addition, in the plane of the diametric, rear recess and are thereby brought into a position biased towards one another.

In a preferred embodiment of the invention, it is provided for the rod to be subjected to heat treatment for the permanent fixing of the bending of the arms into the open position and into a position biased towards one another. This heat treatment which follows on immediately after the specified deformations results in a structural transition and so the scissors-like tool in the open position and in the position biased towards one another experiences, so-to-speak, a rest position, out of which the arms are elastically deflected during bending.

A wire erosion device can be used, in particular, as parting tool; it would, however, also be possible to use other tools of this type, for example a laser beam or an electron beam. It is essential that the parting tool operates linearly so that a separation of the material takes place along this line.

The following description of preferred embodiments of the invention serves to explain the invention in greater detail in conjunction with the drawings.

BRIEF DESCRIPTION OF THE DRAWINGS

FIG. 3: a plan view of the scissors-like tool of FIG. 1;

FIG. 4: a schematic side view of an additional, preferred embodiment of a scissors-like tool with arms bent inwardly at an angle;

FIG. 5: a perspective view of the scissors-like tool of FIG. 5 and

DETAILED DESCRIPTION OF THE INVENTION

Figure 1:
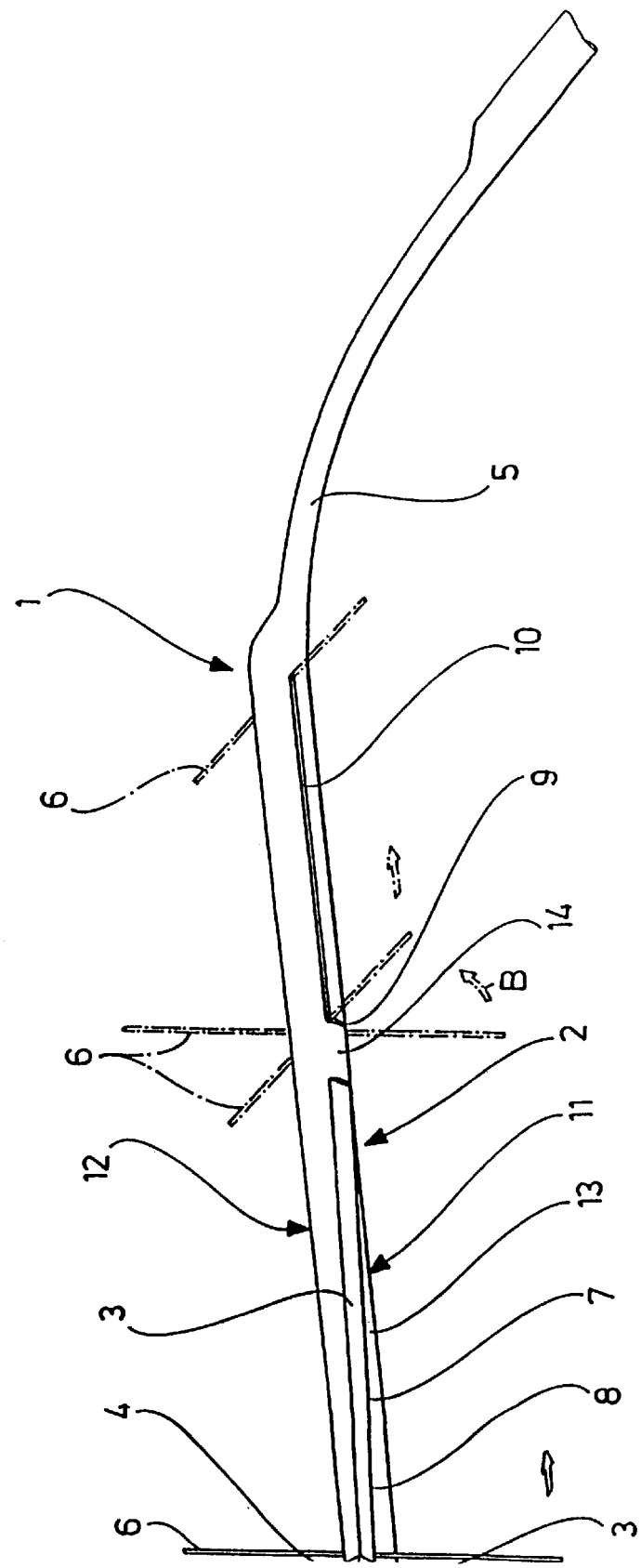
FIG. 1: a side view of a rod with a scissors-like tool, including the illustration of a parting tool in various positions.

The production of a scissors-like instrument starts from a rod or wire 1 consisting of an elastic material, in particular consisting of a metal alloy with pseudoelastic characteristics. This material can, for example, be a nickel-titanium alloy. The external diameter of the wire 1 which has a circular cross section is, for example, in the order of magnitude of 1 mm, where necessary it can even be less.

This wire 1 forms at the same time the pull and push rod of a surgical tubular shafted instrument which is not illustrated in the drawings; this pull and push rod is arranged in the interior of a rigid tube of this instrument and is displaceable in longitudinal direction in relation to this rigid tube, as is known, for example, from WO94/08521 already mentioned.

The front end of this wire 1 is designed in the manner described in the following to form a scissors-like tool 2 which is then positioned at the front end of the tubular shafted instrument and can be opened and closed from the opposite side of the tubular shafted instrument.

First of all, the wire 1 is provided at its circumference with two diametrically opposite flattened areas 3 which extend from the end face 4 over a specific length, for example over a length of 5 mm in the case of a wire 1 having a diameter of 0.7 mm.

In the embodiment illustrated in FIG. 1, the cross section of the wire 1 is weakened, in addition, at a certain distance from the end face 4 over a bending area 5, for example over half the cross section. In this area, the wire may be bent more easily than in the remaining areas, and in the case of a tubular shafted instrument with a bent tube this bending area 5 is positioned in that part of the tube which is bent.

Following this working of the external circumference of the wire 1, various recesses are introduced into the wire, namely with the aid of a tool which produces a material separation along a line. This may be, in particular, a wire erosion device but also beam devices, for example laser beam devices or electron beam devices. In the embodiment of FIG. 1, a wire erosion device is illustrated as an example with a wire-like tool 6 which produces a linear separation cut in the material of the wire 1 in the area of contact with the wire 1 to be worked.

This tool 6 is introduced into the wire 1 diametrically from the end face 4 of the wire 1, namely in such a manner that the diametric, front recess 7 thereby resulting intersects the flattened areas 3 at an acute angle at its lower edge and at its upper edge so that a cutting line 8 is formed.

The diametric, front recess 7 divides the wire 1 into two halves, and this recess 7 extends beyond the flattened areas 3.

At the end of the diametric, front recess 7 which can extend over a length of 5.5 mm, for example, in the case of a wire 1 with a diameter of 0.7 mm, tool 6 and wire 1 are turned about the longitudinal axis of the wire 1 relative to one another, namely through an angle of 90°. This is illustrated in FIG. 1 by arrow B. This means that at the end of the diametric, front recess 7 two transverse recesses 9 are produced in the wire 1 which extend over an angle of 90° and thus each fill a quadrant of the wire cross section. The transverse recesses 9 are located diametrically opposite one another; areas without such transverse recesses which likewise extend through a circumferential angle of 90° remain therebetween.

After the wire 1 has been turned relative to the tool 6, the tool 6 is guided further in the wire 1 and produces a diametric, rear recess 10 which is turned through 90° about the longitudinal axis of the wire in relation to the diametric, front recess 7 and which can, for example, extend over the same length as the diametric, front recess 7. The diametric, front recess 7, the two transverse recesses 9 and the diametric, rear recess 10 divide the wire 1 into two arms 11, 12 which are integrally connected to the remaining part of the wire 1 at the end of the diametric, rear recess 10.

These two arms 11, 12 form the arms of the scissors-like tool 2. In order to actually be able to use these like a pair of scissors, a deformation of the arms is necessary following the introduction of the recesses described.

For this purpose, the two arms are first of all spread apart in the plane of the diametric, front recess 7, namely to such an extent that the inner surfaces 13 of the diametric, front recess 7 no longer overlap one another. Subsequently, the two arms are bent towards one another in the plane of the diametric, rear recess 10, preferably to such an extent that the outer surfaces 14 of the two arms are located in one plane. In this position, which is illustrated schematically in FIG. 6, the arms are thus deflected elastically out of their original rest position in two planes. As a result of heat treatment following this deforming process, this position is fixed, as illustrated, for example, in FIG. 6. This results from a structural transition as a result of the heat treatment process.

Figure 2:
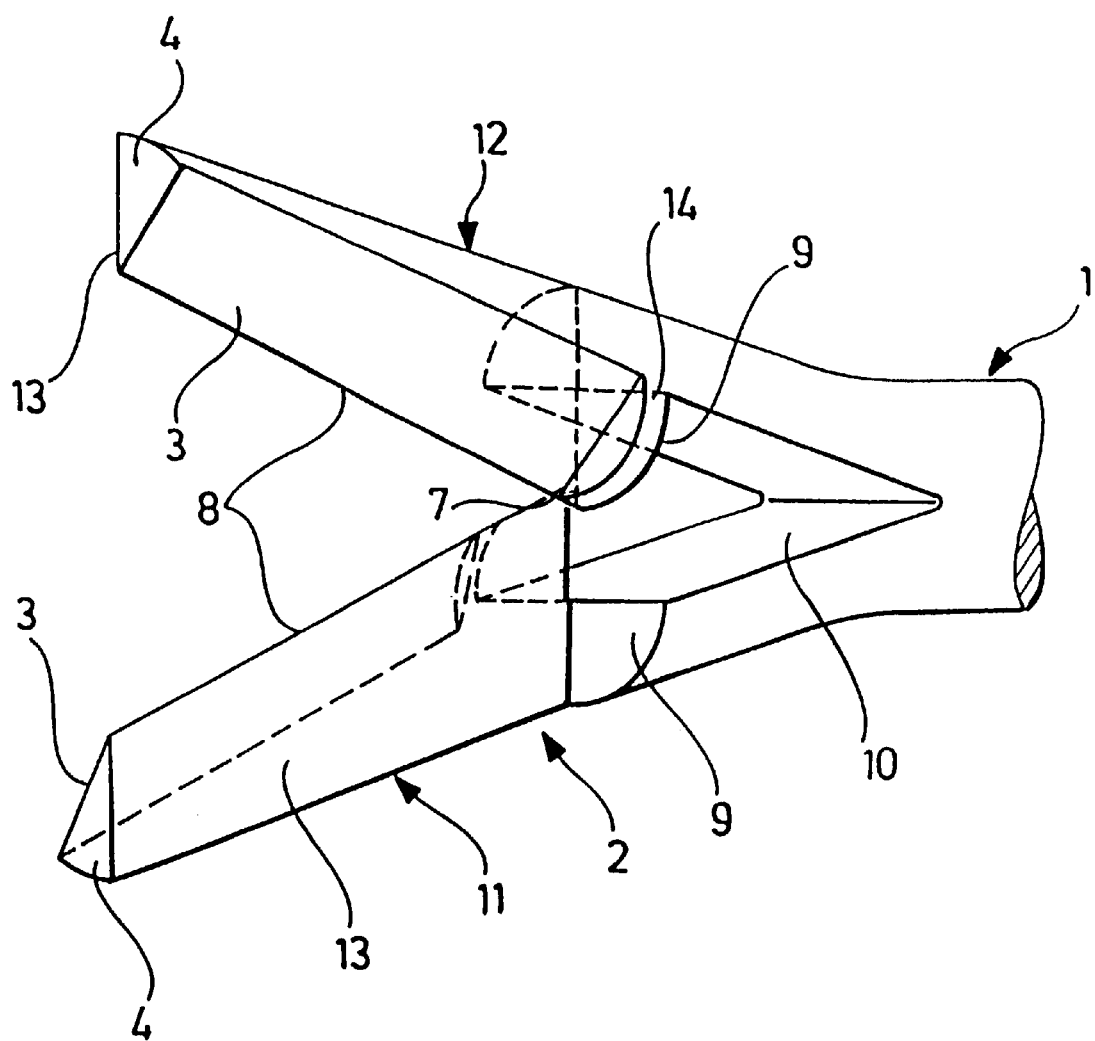
FIG. 2: a perspective side view of the scissors-like tool of a first embodiment in an opened position.
Figure 6:
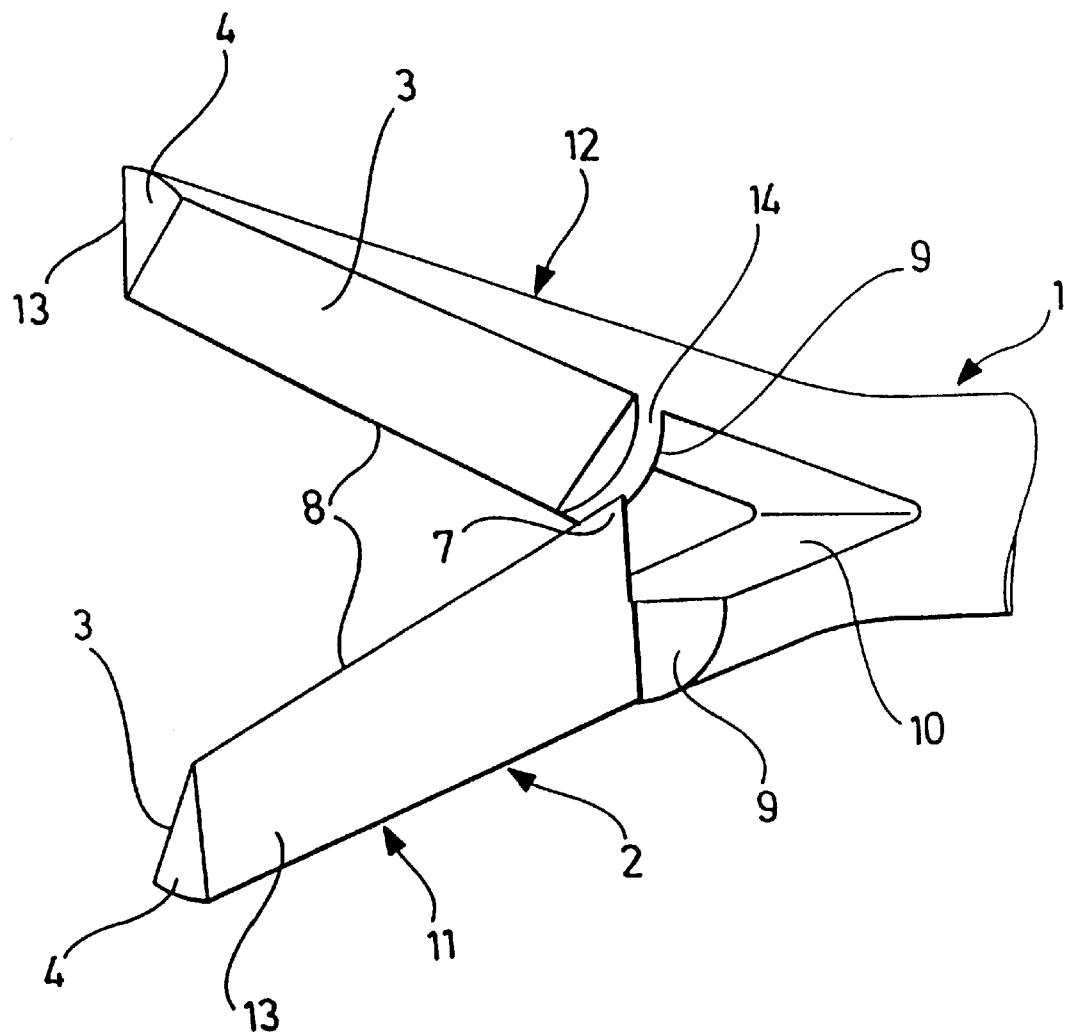
FIG. 6: a view of a scissors-like tool with arms bent up and arms bent towards one another during the permanent fixing in position of these deformations.

This results in a new rest position of the two arms which corresponds approximately to the position in FIG. 6. This rest position is preferably selected such that the two arms still overlap one another very slightly in the spread position. When the two arms are then, as a result of additional elastic bending out and elastic bending back of the arm pivoted laterally outwards, brought back again from the heat treatment position illustrated in FIG. 6 into a position, in which the two arms extend essentially parallel, the inner surfaces 13 of the diametric, front recess 7 abut against one another in the rest position. Their overlapping is minimal, as illustrated in FIG. 2. Moreover, the inner surfaces 13 are pressed elastically against one another so that the two arms 11 and 12 about one another in the region of the cutting lines 8 with a certain bias. This means that the scissors-like tool takes up the rest position shown in FIG. 2 which forms, at the same time, the open position of the tool.

In order to close the scissors-like tool 2, a sleeve is pushed over the wire 1 and this sleeve is displaceable in an axial direction relative to the wire 1. It engages around the two arms 11, 12, in particular, in the region of the diametric, rear recess 10 and causes these to abut on one another to an increasing extent when the sleeve is pushed further along the wire 1, whereby the arms 11, 12 are pivoted elastically into the virtually closed position. In this respect, the inner surfaces 13 of the two arms 11, 12 slide along one another under bias in the region of the cutting line 8; a cutting movement is thus obtained in this region.

After a cut has been carried out, the sleeve displaceable on the wire 1 is withdrawn again so that the arms 11, 12 can return elastically to their rest position, i.e. to the opened position.

The sleeve pushed onto the wire 1 may be a small metal tube in the case of a straight tubular shafted instrument; in the case of a tubular shafted instrument with a bent tube it is favorable when a flexible hose is pushed onto the wire 1 as sleeve, for example a hose consisting of polytetrafluoroethylene. This can be displaced in axial direction between the wire 1, on the one hand, and the surrounding tube, on the other hand, and thereby control the opening and closing movement of the scissors-like tool 2.

In the embodiment of FIGS. 1 to 3 and 6, the arms 11, 12 have been left in their original shape, i.e. they are designed in a straight line.

In the embodiment of FIGS. 4 and 5, the arms are bent an at angle inwardly, in addition, in the plane of the diametric, front recess 7 so that the inner surfaces 13 do not overlap one another in the area of transition to the diametric, rear recess 10 but at a point closer to the end face 4. This makes it possible to design the angle of opening of the two arms so as to be larger; this can be of advantage for certain fields of use. This deformation by bending at an angle is also stabilized by the heat treatment described.

What is claimed is:

1. A scissors-like tool for a surgical instrument, comprising:

a rod comprising elastic material;

said rod having two interconnected arms that are pivotable elastically between a spread open position and a virtually closed position by a sleeve that is axially displaceable relative to said interconnected arms, and which engages around the scissorslike tool, including engaging around an outside portion of said interconnected arms;

said rod further comprising, in order to form said interconnected arms:

(a) a front diametric recess that starts from a free end of said rod;

(b) a rear diametric recess that is turned through approximately 90° about a longitudinal axis of said rod in relation to said front diametric recess; and (c) transverse recesses extending transversely to the longitudinal axis of the rod for connecting said front and rear diametric recesses with one another; wherein:

said transverse recesses each extend over oppositely located quadrants of a cross section of said rod between said front and rear diametric recesses;

two quadrants located between said oppositely located quadrants have no such transverse recesses; and first respective portions of said interconnected arms are permanently bent outwardly with respect to each other in a plane of said front diametric recess.

2. A scissors-like tool as defined in claim 1, wherein:

second respective portions of said interconnected arms are bent towards one another so as to permanently overlap one another in a plane of said rear diametric recess.

3. A scissors-like tool as defined in claim 2, wherein:

said rod comprises two lateral, diametrically opposite flattened areas on an outer side thereof; and said flattened areas form an acute angle with said front diametric recess, and together with an inner surface of said front diametric recess, form a cutting edge.

4. A scissors-like tool as defined in claim 1, wherein:

said rod has a circular cross section.

5. A scissors-like tool as defined in claim 1, wherein:

said rod has two lateral, diametrically opposite flattened areas on an outer side thereof; and said flattened areas form an acute angle with said front diametric recess, and together with an inner surface of said front diametric recess, form a cutting edge.

6. A scissors-like tool as defined in claim 5, wherein:

said rod is formed as a push and pull rod of a tubular shafted instrument; and said rod is displaceable in a tube of the instrument in an axial direction relative thereto.

7. A scissors-like tool as defined in claim 6, wherein:

following the interconnected arms, the rod has a bending area with a reduced cross section.

8. A scissors-like tool as defined in claim 7, further comprising:

a flexible hose arranged on the rod and within the tube as a sleeve engaging around the scissors-like tool.

9. A scissors-like tool as defined in claim 7, wherein:

said first respective portions of said interconnected arms are permanently bent outwardly with respect to each other in a direction of said free end of said rod.

10. A scissors-like tool as defined in claim 7, wherein:

said rod is made in one piece.

11. A scissors-like tool as defined in claim 7, wherein:

said rod consists of a wire.

12. A scissors-like tool as defined in claim 7, wherein:

said front diametric recess extends from said free end of said rod to one of said transverse recesses; and said rear diametric recess extends from the other one of said transverse recesses to a rear portion of said rod.

13. A scissors-like tool as defined in claim 12, wherein:

said two interconnected arms meet at the rear portion of said rod.

14. A scissors-like tool as defined in claim 1, wherein:

said rod consists of an alloy displaying pseudoelastic characteristics.

15. A scissors-like tool as defined in claim 1, wherein:

said rod is formed as a push and pull rod of a tubular shafted instrument; and said rod is displaceable in a tube of the instrument in an axial direction relative thereto.

16. A scissors-like tool as defined in claim 1, wherein:

said interconnected arms are bent at an angle inwardly in a plane of the front diametric recess.

17. A process for the production of a scissors-like tool, comprising the steps of:

a. using a linearly parting tool to introduce a front diametric recess into a rod comprising elastic material, starting from an end face of the rod, to separate the rod into two halves in an area of the front diametric recess;

b. turning the rod through approximately 90° about a longitudinal axis thereof relative to the parting tool at an end of the front diametric recess to produce two transverse recesses extending over approximately 90° about the longitudinal axis;

c. using the linearly parting tool to introduce a rear diametric recess into the rod, by turning the rear recess through approximately 90° about the longitudinal axis in relation to the front diametric recess, and extending the linearly parting tool in the rod towards a rear portion of the rod that is away from the transverse recesses; wherein:

two interconnected arms are formed in the rod as a result of the front and rear diametric recesses; and said two interconnected arms are pivotable elastically between a spread open position and a virtually closed position; and d. permanently bending first respective portions of the two interconnected arms outwardly with respect to each other in a plane of the front diametric recess.

18. A process as defined in claim 17, comprising the further step of:

permanently bending second respective portions of the two interconnected arms towards one another in a plane of the rear diametric recess to bring them into a position biased towards one another.

19. A process as defined in claim 18, comprising the further step of:

heat treating the rod to permanently fix the bending of the second respective portions of the two interconnected arms.

20. A process as defined in claim 18, wherein:

a wire erosion device is used as the parting tool.

21. A process as defined in claim 17, comprising the further step of:

heat treating the rod to permanently fix the outward bending of the first respective portions of the two interconnected arms.

22. A process as defined in claim 21, wherein:

a wire erosion device is used as the parting tool.

23. A process as defined in claim 17, wherein:

a wire erosion device is used as the parting tool.

24. A process as defined in claim 17, wherein:

in said step d, said first respective portions of the two interconnected arms are permanently bent outwardly with respect to each other in a direction of said end face of said rod.

25. A process as defined in claim 17, wherein:

said rod is made in one piece.

26. A process as defined in claim 17, wherein:

said rod consists of a wire.

\* \* \* \* \*